(12) United States Patent
Constantinides et al.

(10) Patent No.: US 6,479,540 B1
(45) Date of Patent: Nov. 12, 2002

(54) COMPOSITIONS OF TOCOL-SOLUBLE THERAPEUTICS

(75) Inventors: Panayiotis P. Constantinides, Gurnee, IL (US); Karel J. Lambert, Woodinville, WA (US); Alexander K. Tustian, Bothell, WA (US); Andrew M. Nienstedt, Seattle, WA (US)

(73) Assignee: Sonus Pharmaceuticals, Inc., Seattle, WA (US)

( * ) Notice: Subject to any disclaimer, the term of this patent is extended or adjusted under 35 U.S.C. 154(b) by 0 days.

(21) Appl. No.: 09/671,753

(22) Filed: Sep. 27, 2000

Related U.S. Application Data
(60) Provisional application No. 60/156,128, filed on Sep. 27, 1999.

(51) Int. Cl.[7] .................. A61K 31/355; C07D 307/77
(52) U.S. Cl. ................... 514/458; 514/937; 514/938; 424/400; 549/407
(58) Field of Search ............... 514/458, 937, 514/938; 424/400; 549/407

(56) References Cited

U.S. PATENT DOCUMENTS

| | | | | |
|---|---|---|---|---|
| 4,439,432 A | * | 3/1984 | Peat | 424/240 |
| 4,551,332 A | * | 11/1985 | Stillman | 424/195.1 |
| 5,041,278 A | * | 8/1991 | Janoff et al. | 424/1.1 |
| 5,583,105 A | * | 12/1996 | Kovacs et al. | 514/11 |
| ,858,398 A | | 1/1999 | Cho | |

FOREIGN PATENT DOCUMENTS

| | | |
|---|---|---|
| WO | WO 95/11039 | 4/1995 |
| WO | WO 95/31217 | 11/1995 |
| WO | WO 98/30205 | 7/1998 |
| WO | WO 99/04787 | 2/1999 |
| WO | WO 00/71163 | 11/2000 |

OTHER PUBLICATIONS

* references cited in specification.*

* cited by examiner

*Primary Examiner*—Amelia Owens
(74) *Attorney, Agent, or Firm*—Christensen O'Connor Johnson Kindness PLLC

(57) ABSTRACT

Tocol-based compositions of charged amphiphilic and water soluble pharmaceutically active compounds or their charged precursors are prepared by forming a tocol-soluble ion pair with an oppositely charged ion-pair forming compound capable of forming a tocol-soluble ion-pair with the active compound.

Also disclosed are novel compounds tocopherolsuccinate-aspartate and tocopherolsuccinate-glutamate, which are useful as ion-pair forming compounds.

61 Claims, 1 Drawing Sheet

COMPOSITIONS OF TOCOL-SOLUBLE THERAPEUTICS

This application claims benefit of No. 60/156,128 filed Sep. 27, 1999.

BACKGROUND AND PRIOR ART

The invention is directed to compositions having an oil phase that contains pharmaceutically active ingredients that are charged amphiphilic or water soluble. The compositions generally comprise tocol-soluble ion pairs in a tocol-based oil of a multiphasic system or a precursor of such a system. The compositions of the invention can be in the form of an emulsion, liquid crystalline gel, self-emulsifying drug delivery system, or a liposomal or niosomal dispersion for oral or parenteral administration, which term is meant to include, for instance, intravenous, subcutaneous, intraperitoneal, intramuscular, pulmonary, intranasal, and topical administration such as transdermal and ocular. Emulsions or microemulsions and self-emulsifying drug delivery systems are the preferred form of the compositions of the present invention.

Emulsions, and emulsification as a composition and method of administration of pharmaceuticals, have a long history in the medical arts. A recent advance was the use of α-tocopherol or other tocopherols, tocotrienols or derivatives thereof as a solvent to dissolve certain drugs at high enough concentrations to be therapeutically useful. TPGS (60 -tocopherol polyethyleneglycol 1000 succinate) for administration of a therapeutic was claimed by Biogal (U.S. Pat. No. 5,583,105) following disclosure in trade publications of the utility of TPGS as a bioavailability enhancer for drug delivery (Sokol, et al. The Lancet 338:212–215, 1991). Vitamin E and tocopherol acetates and succinates, including TPGS, were recently found useful in pharmaceutical formulations as solubilizers and co-solvents for the administration of medicaments (Dumex WO/95,31217 and Liposome Company, U.S. Pat. No. 5,041,278). Other patents disclose that tocopherols are excellent solvents for the peptide cyclosporin (Klokkers WO 95/11039), and for certain steroids (Peat, U.S. Pat. No. 4,439,432). Stillman (U.S. Pat. No. 4,551,332), and Hermes Pharma (EP 019817) described composition in which steroids and antibiotics, or ubiquinones, respectively, were co-solubilized in Vitamin E as pharmaceutical formulations.

Subsequent disclosures by Sonus Pharmaceuticals (WO 98/30205); Sherman (WO 97/22358; WO 98/30204) and Danbiosyst (WO 97/03651; WO 99/04787) expanded this new appreciation of tocopherols and tocotrienols as a solvent for delivery of hydrophobic medicaments, particularly when combined with TPGS, phospholipids, and certain co-solvents and emulsifiers.

The benefits of emulsions are several. In general, emulsification can lead to reduced toxicity when compared to aqueous solutions of the drug. Extreme conditions of pH or ionic strength are required to solubilize some drugs in aqueous solutions. Also, sustained release has been observed from emulsions formed as a blood pool or intra-tissue depot, from which the active agent is progressively released with desirable increased efficacy or duration of treatment. In other cases, a high plasma peak concentration (Cmax) can be obtained without undue risk to the patient. Finally, the stability of selected drugs in the oil phase may be improved when compared to aqueous solutions of the same drug. Emulsions in tocopherols, tocotrienols or derivatives thereof have the added advantage that the emulsion itself may be therapeutic for certain conditions.

However, only selected lipophilic active agents are highly soluble in tocopherols and tocotrienols. Furthermore, lipophilic agents that are charged tend to remain associated with the water or plasma, where they may be subject to degradation, even while residing in part in the oil phase. Finally, some water-soluble agents or amphiphilic agents that could benefit from the advantages of a tocopherol or tocotrienol formulation are not readily soluble in these oils.

It would thus be desirable to provide pharmaceutical compositions in which a charged amphiphilic or water soluble active agent is partitioned into the tocol oil phase of a multiphasic system.

One approach to improve the oil solubility of such ingredients is to covalently modify the active agent so as to render it more lipophilic. Fatty acid- or lipid-drug conjugates have been disclosed as a means of rendering water-soluble drugs more lipophilic, more readily absorbable through various mucosal membranes, such as the intestinal, corneal and dermal, and for targeting of drugs (NexStar U.S. Pat. Nos. 6,024,977; 5, 827,819; 5, 543,389; 5,543,390; 5,840,674; 5,543,391; 5,256,641; 5,149,794).

Another solution has been to use liposomes, reverse emulsions or water/oil/water multiple emulsions, in which the drug may be contained in an aqueous phase dispersed in the oil matrix or, in the case of liposomes, enclosed within a lipid bilayer. These formulations are particularly valuable for water-loving drugs and macromolecules but may not provide the advantages of solubilizing the drug directly in the oil. In addition there are physical stability considerations of such systems.

SUMMARY OF THE INVENTION

The invention comprises a pharmaceutical composition comprising a tocol as a solvent and a tocol-soluble ion pair of two oppositely charged compounds, one of the said compounds being a charged pharmaceutically active agent or a charged precursor of the active agent and the other being an oppositely charged compound capable of forming a tocol-soluble ion pair with the pharmaceutically active compound. In cases of multiply charged pharmaceutically active compounds or precursors of charged pharmaceutically active compounds at least one charge on the active agent is available for ion-pairing. The invention also relates to processes for preparing such compositions.

DETAILED DESCRIPTION OF THE INVENTION

Figure 1:
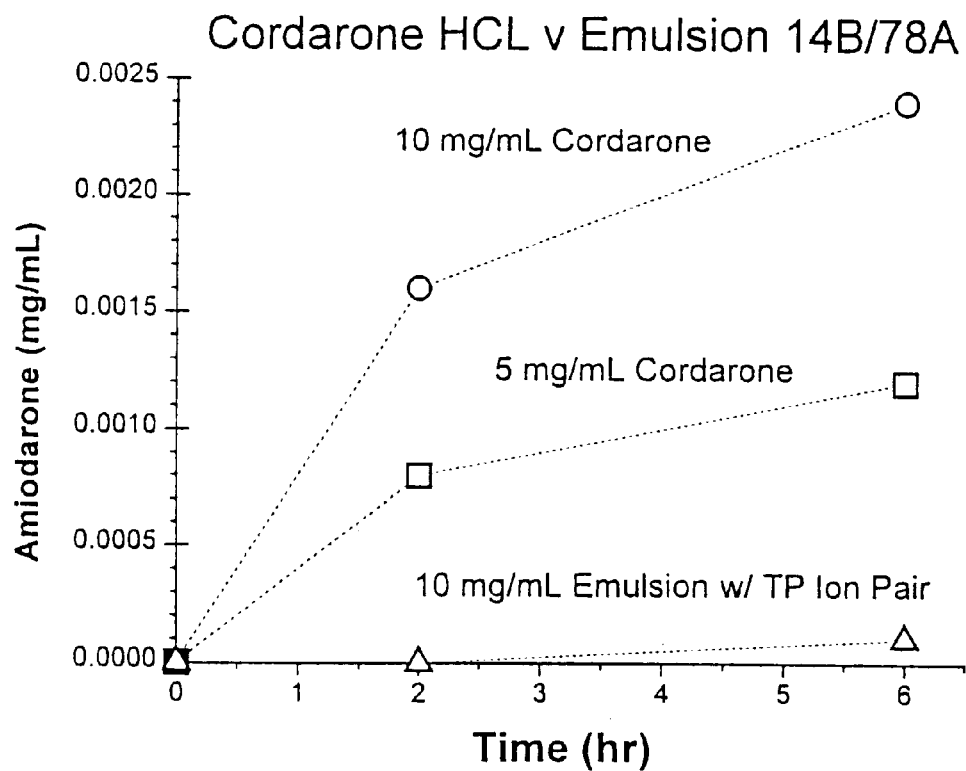
FIG. 1 is a graph illustrating the dialysis of amiodarone.

The present invention is directed to formulations or compositions of those drugs which are amphiphilic or water soluble by virtue of having a substituent ionic charge, for example a cation formed from a secondary amine (a base), or an anion formed by dissociation of a carboxyl, phosphate or sulfate (an acid). These drugs may be rendered tocol-soluble by the formation of an ion-pair between the drug and an oppositely charged molecule. The active agent of the composition must be more soluble in the tocol oil in the form of an ion pair than without it. Thus, formation of the ion-pair results in substantial improvement in the solubility of the active agent in the tocol oil.

To better aid in understanding the invention, the following definitions are offered:

Tocopherols: tocopherols are a family of natural and synthetic compounds. d-α-tocopherol, also known as Vitamin E, is the most familiar member of this class of compounds and has the following chemical structure (Scheme I):

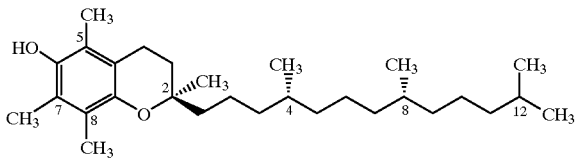

The molecule contains three structural elements, a chroman head with a phenolic alcohol and a phytyl tail. Not all tocopherols have three methyl groups on the chroman head. The simplest member of this group, 6-hydroxy-2-methyl-2-phytylchroman contains no methyl groups on the chroman ring, and is sometimes simply referred to as "tocol". However, the terms "tocols" and "tocol" is used herein to represent a broader class of compounds. Other members of the tocopherol class include α-, β-, γ-, and δ-tocopherols and Trolox® (6-hydroxy, 2,5,7,8-tetramethylchroman-2-carboxylic acid) and its desmethyl analogs. In addition to their use as a primary solvent, some tocopherols and their derivatives are useful as a therapeutic agents.

Tocotrienols: tocotrienols have structures related to the tocopherols but possess a 3, 7, 11 triene "tail". The structure of d-α-tocotrienol is shown in Scheme II.

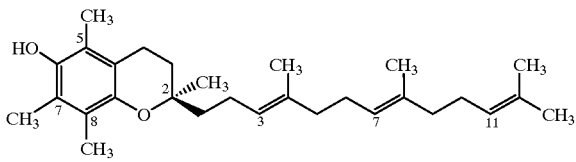

Again, as is the case for the tocopherols, not all tocotrienols have three methyl groups on the chroman head. There are four major tocotrienols, α-, β-, γ-, and δ-tocotrienols.

Tocols: "Tocols" is used herein in a broad sense to indicate the family of tocopherols and tocotrienols and derivatives thereof, including those common derivatives esterified at the 6-hydroxyl on the chroman ring. This use of the term "tocols" is appropriate since all tocopherols and tocotrienols are fundamentally derivatives of the simplest tocopherol, 6-hydroxy-2-methyl-2-phytylchroman (sometimes referred to as "tocol").

Tocol-Soluble: Refers to the property of certain molecules characterized as being soluble directly, or with the aid of a co-solvent, in a tocol. As an operative definition, the most useful way to determine tocol solubility is to dissolve the compound of interest in a tocol or to use a co-solvent such as ethanol.

Amphiphilic: A molecule that is both oil and water soluble.

Lipophilic: Literally, fat-loving, referring to the property of certain molecules characterized as soluble in triglyceride oils, hydrocarbons or waxes.

Ion Pair: A neutral pair formed between two oppositely charged compounds.

Tocol-Soluble Ion Pair: An ion pair formed between two oppositely charged compounds and which is soluble in tocols.

Biocompatible: Capable of performing functions within or upon a living organism in a manner that does not terminate or excessively disable the life of the organism, i.e. without undue toxicity or harmful physiological or pharmacological effects.

Multiphase System: As used herein, this term refers to a system where one or more phases is (are) dispersed throughout another phase, which is usually referred to as the continuous phase or vehicle, or a precursor thereof. Emulsions, microemulsions and other nanoparticulates, including liposomes and niosomes, are examples of multiphase systems.

Liposome: A lipid bilayer vesicle formed spontaneously upon dispersion of lipids/phospholipids in water. "Liposome" is also defined as a vesicular structure consisting of hydrated bilayers.

Niosome: In analogy to a liposome, a niosome is a nonionic surfactant vesicle. Classes of commonly used non-ionic surfactants include polyglycerol alkylethers, glucosyl dialkylethers, crown ethers and polyoxyethylene alkyl ethers and esters.

Micelle: Organized aggregates of one or more surfactants in solution.

Emulsion: A colloidal dispersion of two immiscible liquids, such as oil and water, in the form of droplets. The internal phase is also termed the dispersed phase and the external phase is termed the continuous phase. The mean diameter of the dispersed phase, in general, is between about 0.1 and about 5.0 microns, as is commonly measured by particle sizing methods. Emulsions in which the dispersed phase and continuous phase have different refractive indexes are typically optically opaque. Emulsions possess a finite or limited stability over time, and can be stabilized by the incorporation of amphiphilic excipients known as surfactants and by viscosity modifiers.

Microemulsion: A thermodynamically stable, isotropically clear dispersion of two immiscible liquids, stabilized by an interfacial film of surfactant molecules. Microemulsions have a mean droplet diameter of less than about 200 nm, in general between about 10–100 nm and are typically self-assembling.

Tocol microemulsion: A thermodynamically stable, translucent or clear dispersion of a tocol oil in water, stabilized by an interfacial film of surfactant molecules. Tocol microemulsions have a mean droplet diameter of less than about 200 nm, in general between about 50 and about 100 nm, and typically are not self-assembling, but require heat or increased shear to assemble due to the high viscosity of the tocol oil.

A highly preferred form of the invention for drug delivery is a "tocol microemulsion". These vehicles for drug delivery are translucent and isotropic, of small mean droplet diameter, preferably less than about 150 nm, even more preferably less than about 100 nm, and most preferably from about 30 to 90 nm. They possess high drug solubilization capacity (a relative measure for each individual drug), and most characteristically have extended or indefinite stability on storage by virtue of their thermodynamic stability, which is preferably greater than 1 year, even more preferably greater than two years or more. The microemulsions of the current invention have a surfactant to oil ratio of about 1:1 to 1:5, preferably from about 1:1 to 1:2 and are frequently formulated with one or more co-solvents or co-surfactants to improve processing. Unlike vegetable oil microemulsions, which form spontaneously, tocol microemulsions are formed by homogenization in a high-shear device because of the extremely high viscosity of these excipients. However, once formed, they are essentially transparent or translucent, and highly stable. They preferably exhibit no particle size growth over a typical pharmaceutical shelf life of one year or more.

Self-Emulsifying Drug Delivery Systems (SEDDS):

In the absence of an aqueous phase, mixtures of oil(s) and non-ionic surfactant(s) form clear and isotropic solutions that are known as self-emulsifying drug delivery systems (SEDDS). They have successfully been used to improve lipophilic drug dissolution and oral absorption. Such systems are essentially precursors of emulsion-type multiphasic systems.

Active Agent: A compound or precursor thereof, natural or synthetic, with an established therapeutic/pharmacological activity in animals and humans. Relevant to this invention are compounds that are relatively soluble in tocols and compounds that are relatively insoluble in tocols.

Polyelectrolyte: A natural or synthetic molecule with multiple ionizable groups. A polyelectrolyte can have multiple anions, multiple cations or a combination of both. Examples include peptides, polypeptides, proteins, saccharides and polysaccharides, polynucleotides and nucleic acids.

Pharmaceutically active ingredients that may be employed in the compositions of this invention are those that are charged amphiphilic or water soluble. These include, for instance, therapeutic amines or bases, acids and zwitterions. Preferred classes of compounds include carboxylic acids, polycarboxylic acids, amines, polyamines, peptides, polypeptides, proteins, nucleosides, nucleotides, polynucleotides, saccharides, polysaccharides, polymers, and other charged polyelectrolytes. Most preferred are amines, peptides and polypeptides.

Some examples of preferred active ingredients for use in this invention are macrolide antibiotics such as clarithromycin and erythromycin, anthracycline antibiotics such as doxorubicin and daunorubicin, camptothecin and its analogs (such as camptothecin, topotecan, irenotecan and derivatives thereof), quinolone antibiotics such as ciprofloxacin, clinafloxacin, levofloxacin and moxifloxacin, amiodarone and its analogs, angiotensin-converting enzyme (ACE) inhibitors such as enalapril, enalaprilat, linosopril and their analogs, biogenic amines such as histamine, serotonin, tryptophane, epinephrine and analogs or derivatives thereof, the antineoplastics mitomycin and bleomycin and their analogs, and vincristine, nitrogen mustards, and nitrosourea and their analogs. Other chemotherapeutic agents may be used, as may antibiotics (antiviral, antibacterial, antihelminthic, antiplasmodial, or antimycotic), analgesics and local anesthetics, antidepressants anxiolytics, antipsychotics, sedatives, hypnotics, hormones, steroids, cytomedines or cytokines, anti-histamines, anti-allergics, steroids, vaccine adjuvants and epitopes, immunosuppressive agents, vascular tonics, coronary drugs, vasodilators, anti-arrhythmics such as amiodarone, calcium antagonists, cardiac glycosides, antidotes, non-steroidal anti-inflammatory drugs, oligonucleotides, oligopeptides, antiemetics, motion sickness drugs, and migraine therapeutics.

Specific examples of active ingredients that may be used in the compositions of this invention include dihydroergotamines, epinephrine, adenosine, hydralazine, pipamazine, pyridoxine, prednimustine, propanolol, phenobarbital, amiodarone, miconazole, secobarbital, trimethoprim sulfamethoxazole, cytarabine, amphotericin B, diltiazem, verapamil, diazoxide, ketorolac, pentobarbital, phenyltoin, esmolol, capsaicins, oxytetracycline, chlorodiazepoxide, dimenhydrinate, benzodiazepines such as diazepam, fenoldopam, nitrazepam, flurazepam, lorazepam, estazolam, flunitrazepam, triazolam, alprazolam, midazolam, temazepam, lermetazepam, brotizolam, clobazam, oxazepam, clonazepam, thiethylperazine, nicardipine, haloperiodol, tobramycin, ciprofloxacin, clinafloxacin, levofloxacin, moxifloxacin, fluoxetine, metronidazole, doxepin, doxycycline, chloramphenicol, acyclovir, idoxuridine, dynorphine, tromantadine, tranylcypromine, meconazole, nystatin, metronidazole, tinidazol, diclofenac, piroxicam, morphine, Selegiline, lidocaine, buprenorphine, buspirone, metoclopramide, granisetron, tropisetron, ondansetron, chonemorphine, cinnarizine, ceftriaxone, eprosartan, ganciclovir, betamethasone acetate, methylprednisolone acetate, prednisolone, sumatriptan, hydrocortisones, ibuprofen, methocarbamol, resveratrol, retinoids, carotenoids, tamoxifen, decarbazine, Ionidamine, piroxantrone, chloroquine, streptomycin, kanamycin, gentamycin, dehydrostreptomycin, amikacin, chloropromazine, imipramin, suramin, perhexilene, methotrexate, sulmazol, leupeptin, methylamine, colchicine, pyridoxine, acetaminophen, desipramine, biperiden, dibenzepine, alprenolol, opipramol, propranolol, chlorpheniramine, clonixin, desipramine, n-acetyldesipramine, imipramine, chlomipramine, amitryptyline, sertraline, perazine, thioridazine, carbamazepine, promazine, amantadine, memantine, isoproterenol, methadone, lignocaine, pentacaine, nalorphine, trimetazidine, morphine-6-O-β-d-glucuronide, sulmazol, and phenothiazine.

Compositions of this invention containing tocol-soluble ion pairs are useful to formulate and deliver biogenic amines or their amino acid or peptide precursors. Biogenic amines are those cell signaling or transmitter molecules produced by the body which contain a free amine. In some cases the precursor is also efficacious, for example the amino acid tryptophane which is metabolized into serotonin, an active cell signaling and neurotransmitter molecule. Cytomedines comprise a broader class of ligands that interact with cellular receptors to evoke a biological response.

Benefits have also been reported for the administration of tocotrienols or tocopherols for therapy of cardiovascular disease. Compositions of this invention including active agents such as amiodarone, persantine or adenosine in tocol-based emulsions may be useful for bolus or IV drip infusion as a vascular tonic in the treatment of myocardial infarction or for oral administration.

Where it is desirable to shift the partition coefficient so that more of the drug is contained in an oil phase, for example for slow release, the teachings of the present invention offer a useful solution. By delivering the active compound in the form of an emulsion, the release time of the active compound in the blood or tissue can be extended. Reducing the peak concentration ($C_{max}$) for the free amine can minimize or modulate systemic or non-specific toxic or adverse events.

Other lipophilic active ingredients can be included in the compositions of this invention, so as to provide additional or complementary effects to the active ingredient present as part of the tocol-soluble ion pair. For instance if the active ingredient of the ion pair is a chemotherapeutic or oncolytic agent, the composition may contain other chemotherapeutics that are soluble or that can be solubilized in tocols, such as qmonafide, illudin S, 6-hydroxymethylacylfulvene, bryostatin 1, 26-succinylbryostatin 1, palmitoyl rhizoxin, penclomedine, interferon-alpha, angiogenesis inhibitor compounds, cisplatin hydrophobic complexes such as 2-hydrazino-4,5-dihydro-1H-imidazole with platinum chloride and 5-hydrazino-3,4-dihydro-2H-pyrrole with platinum chloride, vitamin A, vitamin E and its derivatives, particularly tocopherol succinate, vinblastine, 5-fluorouracil, methotrexate, edatrexate, muramyl tripeptide, muramyl dipeptide, lipopolysaccharides, 9-β-d-arabinofuranosyladenine ("vidarabine") and its 2-fluoro derivative.

Other useful therapeutic agents for inclusion in the tocol-soluble ion pairs of this invention may be selected on the basis of their amphiphilicity and charge as a function of pH, by their partition coefficient in buffer:octanol, or by their tocol solubility. As an operative definition, preferred candidates are those for which tocol solubility can be shown experimentally to increase in the presence of an ion pair forming compound by measuring drug solubility in the tocol oil with and without the ion-pair. For screening, we have prepared the free base of a drug with an amine functionality and dissolved the free base and vitamin E succinate directly in tocopherol with heat. In other cases we have used ethanol or another volatile co-solvent to initially dissolve the active agent and its ion pair in a tocol, and then evaporated the ethanol. Ion pairs that are not soluble in the tocol of choice readily precipitate or crystallize by these methods. Limits of solubility may also be established by preparing a series of samples containing increasing amounts of the compound in a constant molar mass of tocol. After direct dissolution, or after evaporation of residual ethanol or other volatile solvent used as a co-solvent, the critical limit of solubility ($S_c$) of the compound in the tocol of choice can be determined with accuracy.

Relatively non-volatile co-solvents such as PEG-400, benzyl benzoate, benzyl alcohol, glycerol, glycerol-, propylene glycol- and polyethylene glycol-based esters (oils) that are commercially available under different trade names such as Capmul® MCM (glyceryl mono-/di-caprylate/caprate), Captex® 355 (caprylic/capric triglycerides from coconut oil), Captex® 200 (propylene glycol dicaplylate/dicaprate), Labrafil® M1944 (primarily oleic acid polyglycolyzed glycerides from apricot kernel oil), Labrasol® (caprylate/caprate polyglycolyzed glycerides from coconut oil), Myvacet® (distilled acetylated monoglycerides), Lauroglycol® (propylene glycol mono-/di-laurate), propylene essential lipids (as in U.S. Pat. No. 5,716,928) such as allspice berry, fennel, amber essence, anise seed, arnica, balsam of Peru, basil, bay leaf, parsley, peanut, benzoin gum, bergamot, rosewood, cajeput, marigold, camphor, caraway, cardamon, carrot, cedarwood, celery, chamomile, cinnamon, citronella, palm oils, sage, clove, coriander, cumin, cypress, eucalyptus, aloe, fennel, fir, frankincense, garlic, geranium, rose, ginger, lime, grapefruit, orange, hyssop, jasmine, jojoba, juniper, lavender, lemon, lemongrass, marjoram, mugwort, watercress, mullen, myrrh, bigarde neroli, nutmeg, bitter orange, oregano, patchouly, pennyroyal, primrose, retinols, papaya, pepper, peppermint, poppyseed, petitegrain, pine, poke root, rosehip, rosemary, sandalwood, sassafras, spearmint, spikenard, hemlock, tangerine, tea tree, thyme, vanilla, banana, coconut, vetivert, wintergreen, witch hazel, ylang ylang extract, or synthetic analogs, also β-carotene, carotenoids, quinones, menadiones, lycopene, crown ethers, tributyrin, 1-methyl-2-pyrrolidinone, dimethylsulfoxide, polyvinylalcohol, polyvinylpyrrolidinone, phenol, cholesterol, astaxanthins, phospholipids, polyoxyethylated phospholipids, secondary tocols, Amifat® P30 (glyceryl monopyroglutamate monooleate), surfactants such as Cremophor® EL (polyoxyethylated castor oil), Poloxamer 407®, also lnown as Pluronic® F-127 (polyoxyethylene/polyoxypropylene copolymer), lecithin, bile acids, palmitoyl carnitine, fatty acids, Transcutol® (diethylene glycol monoethyl ether) and mixtures thereof, can be used in the compositions of this invention.

For use in forming ion pairs with cationic drugs, the preferred method is to select one or more charged derivatives of a tocol from the list: vitamin E succinate (VESA), vitamin E phosphate, and other charged tocopherol esters, amino acid derivatives such as tocopherol aspartate and glutamate, and other tocopherol ester or amide derivatives such as those disclosed herein or by Senju Pharmaceuticals (U.S. Pat. No. 5,606,080 or PCT WO 99/22818). For example, tocopherol succinate as the free acid (anionic) can be used to complex clarithromycin or amiodarone as the free base (cationic) to form a tocol-soluble neutral ion pair. In an oil phase of low dielectric constant, these ion pairs are highly stable once formed. Other tocol-soluble ion pair forming compounds include $C_2$–$C_{25}$ tocol-soluble carboxylic acids (preferably the fatty acids) such as acetic, propionic, butyric, valeric, valproic, caprylic, caproic, lauric, myristic, palmitic, oleic, palmitoleic, stearic, linoleic, linolenic, arachidic and arachidonic acid; and include $C_2$–$C_{25}$ acyl amines such as stearylamine, alkyl phosphates such as decyl and hexadecyl phosphate, other charged lipids such as cholesterol analogs, particularly cholesterol esters such as cholesterol sulfate and cholesterol hemisuccinate and succinate, bile acids, phospholipids such as phosphatidic acid, phosphatidylserine, phosphatidylglycerol and diphosphatidylglycerol (cardiolipin), phosphatidylinositol, sphingolipids such as sphingomyelin, cationic lipids such as, N-[1-(2,3-dioleoyloxy]-N, N,N-trimethylammonium chloride (DOGMA), N-L-arginylphosphatidyl-ethanolamine, and 1,2-Diacetyl-3-dimethyl-and trimethyl- ammonium propane, retinoids, vitamin A, D or K esters, and charged biosurfactants such as the Amisoft® line of glutamates available from Ajinomoto (Tokyo, Japan) and ascorbyl palmitate.

In the case of anionic drugs, a preferred composition contains tocopheramine. Other positively charged ion pair candidates include stearylamine and sphingomyelin.

In the case of zwitterionic drugs, more ingenuity is required, but it is well within the scope of this invention to use multiply charged species so as to neutralize the polarity of the target molecule. For example, esterified fatty acids such as glutamyl stearate can be used to pair with drugs containing both an anionic and cationic functional group.

The compositions of the current invention may be emulsions, microemulsions, self-emulsifying systems, liposomal and niosomal dispersions, gels or liquid crystalline mesophases or their precursors. The preferred forms of the invention are oil-in-water emulsions, microemulsions and self-emulsifying drug delivery systems for oral or parenteral administration of an active agent. Examples of multiphasic systems having two or more phases include oil-in-water and water-in-oil emulsions and microemulsions, and multiple emulsions of the oil-in-water-in-oil and water-in-oil-in-water structure.

Therapeutic applications of the formulations envisaged here include the delivery of drugs effective in the treatment of cancer, pain, infections, atherosclerosis, kidney disease, for suppression of rejection of transplanted organs, and for other medical arts.

Specific embodiments of this invention are described herein. However, variations and modifications of these embodiments can be effected without further inventive step, within the teachings and scope of the invention as described herein.

EXAMPLES

Example 1

Tocol-soluble Ion Pair Formulation of Clarithromycin for Intravenous Administration.

Clarithromycin is a macrolide antibiotic widely prescribed for a variety of bacterial infections. Other important members of this class of drugs include azithromycin and erythromycin. Macrolide antibiotics are primarily given orally, although intravenous dosing is indicated in some cases. Macrolides are known for causing venous irritation/pain on injection, so they are generally given in dilute (2 mg/mL) solutions by slow infusion (total daily doses can be in gram quantities).

Clarithromycin free base is poorly water soluble but can be solubilized in water as a water-soluble salt, for example the lactobionate or glucoheptonate, solutions of which display the aforementioned venous irritation. The relative lipophilicity of clarithromycin has led various investigators to propose a variety of lipid dispersed systems, such as liposomes, mixed micelles, and oil-in-water (o/w) emulsions which might shield the drug from contact with sensitive tissues at the injection site. To date, however, none of these has advanced as far as clinical development.

In particular, the amino group can be exploited through lipophilic ion pairing to capture the drug in the oil phase of an o/w emulsion. Lovell et al; (1994), Less-painful intravenous administration of clarithromycin, Int. J. Pharmaceutics 109: 45–57, developed a triglyceride emulsion using fatty acids as lipidic counterions, which displayed roughly a two-fold reduction in pain response in the animal models chosen.

Clarithromycin was obtained as the free base from Wockhardt (Delhi, India). Vitamin E Succinate (VESA) was obtained from Eastman (Freeport Tenn.). Capmul® MCM was obtained from Abitec (Janesville Wis.); Poloxamer® 407 (Pluronic® F-127) from BASF (Parsippany N.J.); PEG-400 from Spectrum Chemicals (Gardenia Calif.), and d-δ-tocopherol from Sigma Chemicals (St Louis MO). An oil phase consisting of d-δ-tocopherol and Capmul MCM was prepared using 2 parts of δ-tocopherol. Surfactant and clarithromycin were then added as shown in the table below. Dry ethanol was used to dissolve the components at 70° C. and the ethanol was then removed under vacuum. A clear amber oil resulted, but upon cooling, oblong, "casket-lid" crystals of clarithromycin were observed. A tocol-soluble ion pair of this compound was then produced by addition of a stoichiometric equivalent of Vitamin E succinate (VESA) as the free acid. On re-dissolution in ethanol and cooling no crystals formed. The clarithromycin was now sufficiently soluble in the tocopherol oil to allow subsequent preparation of the emulsion. The oil was then re-heated to 45° C. and degassed immediately prior to emulsification as described below.

| Component | Weight in Oil Phase | Final Percent (%) |
| --- | --- | --- |
| d-δ-tocopherol | 2.53 gm | 5.0% |
| Capmul MCM | 1.28 gm | 2.5% |
| Poloxamer 407 | 2.98 gm | 3.0% |
| Clarithromycin | 0.53 gm | 0.5% |
| Vitamin E Succinate | 0.45 gm | 0.9% |

The aqueous phase, consisting of 40 mL of 5 mM citrate TEA buffer, pH 6.8, was brought to 45° C. before addition to the oil phase. Upon addition, the resultant mixture was mixed vigorously to loosen any adherent oil on the walls of the flask. This suspension was then placed in a vessel and processed in a C5 homogenizer (Avestin, Ottawa Calif.) for 3 min with continuous recycling. Processing conditions were 45° C. feed temperature, 20 kpsi processing pressure and 120 mL/min flow rate. A heat exchanger set at 22° C. was placed at the exit port to remove excess heat generated in the homogenizer. The temperature in the feed vessel was measured at 44° C. during steady state homogenization. Following processing, the emulsion was collected and cooled to room temperature. It was then terminally sterilized by filtration through a 0.2 μm filter and had a mean droplet diameter of less than 52 nm when measured on a Nicomp 370 photon correlation spectrophotometer (Particle Sizing Systems, Santa Barbara Calif.).

Similar emulsions can be made for other lipophilic drugs that exist as a free base, for example doxorubicin or erythromycin. Optionally, other oils as discussed earlier in the specification and preferably Lauroglycol® may be used in place of Capmul MCM in the formulation. Miglyol 812 (caprylic/capric triglycerides) and like oils may also be used.

Example 2

Stability of Clarithromycin Formulation

The physical and chemical stability of the formulation of Example 1 at 4° C. was followed for 6 months. No detectable physical change in the microemulsion incorporating a tocol-soluble ion-pair could be detected by gross examination or by measuring emulsion droplet size using standard particle sizing methods. Likewise, no detectable degradation of clarithromycin could be detected by HPLC. In contrast, a solution of the lactobionate salt had degraded by about 50% over the same time period. Thus, the microemulsion when stored at 4° C. remained stable for at least 6 months.

Example 3

Amiodarone as a Tocol-soluble Ion Pair Compound

Amiodarone is a Class III anti-arrhythmic for care of patients suffering or at risk of heart attack. Since 1977, it has been administered as an aqueous solution of the HCl salt in 10% Tween 80 and 2% benzyl alcohol under the tradename Cordarone® IV.

Amiodarone was purchased as the HCl salt (Sigma Chemicals, St Louis Mo.). The free base was prepared by dissolving the drug in chloroform and washing the organic phase with saturated sodium bicarbonate. The drug in the organic phase was then recovered as a pale yellow oil. An emulsion containing 12 mg/mL amiodarone as the free base was then formulated as follows:

| Component | Weight in Oil Phase | Final Percent (%) |
| --- | --- | --- |
| d,1-a-tocopherol | 1.0 gm | 2.0% |
| TPGS | 1.6 gm | 3.2% |
| Poloxamer 407 | 0.25 gm | 0.5% |
| Amiodarone (free base) | 0.6 gm | 1.2% |
| Vitamin E Succinate | 0.5 gm | 1.0% |
| PEG-400 | 3.0 gm | 6.0% |
| Buffer to pH 5.0 | | qs to 50 mL |

The formulation uses a molar equivalent of amiodarone as the free base and Vitamin E succinate as the free acid to form the tocol-soluble ion pair in the tocol oil before processing. Following homogenization at 47° C. for 5 min, a translucent microemulsion was obtained with a mean particle size of 71 nm. Other anions that are therapeutic for heart disease, for example the free fatty acids linolenate, eicosapentaenoate or docosahexaenoate from castor oil, were also useful as tocol-soluble ion pairs with amiodarone and can be used in the form of an oral drug supplement for maintenance therapy.

Mice were then dosed with emulsified amiodarone versus the commercially available amiodarone solution (Cordarone IV, Wyeth Laboratories). Before use, Cordarone was diluted 1:5 with 5% dextrose in water for injection. Animals receiving the commercial solution at 100 mg/kg lost coordination, mobility, and experienced prolonged respiratory disturbance. At an equivalent dose, the emulsion was tolerated much better than the commercially available solution.

Example 4

Effect of Formulation on Amiodarone Blood Pool Levels

Amiodarone as the free base was formulated in an emulsion (A) with tocopherol phosphate and was compared with amiodarone HCl with Tween 80 and benzyl alcohol as a free solution (B). The comparison involved injection of mice with equal amounts of the drug in a bolus volume, and then sacrificing the mice at T=6 hr to determine the blood levels of drug by HPLC. The data demonstrate that blood levels of emulsified drug fall more slowly than those of free or solubilized drug, suggesting that the emulsion composition is present as a blood pool and may have improved therapeutic effect.

| Treatment (n = 6) | Blood Level ($\mu$g/mL) |
|---|---|
| A | 4.79 ± 1.37 |
| B | 1.35 ± 0.41 |

Significant levels of drug metabolites in the animals treated with solubilized amiodarone HCl were detected, but low levels in animals treated with emulsion. This suggests that hepatic uptake in the case of the soluble form of drug is a principal cause of the low blood levels, and that the liver is responsible for the rapid clearance from blood followed by the appearance of metabolites in blood. Because hepatotoxicity is a major concern with this drug, the results presented in this invention suggest a benefit from the use of an emulsified formulation of amiodarone.

Example 5

Relative Release Rates for Amiodarone HCl Versus Amiodarone Tocol-soluble Ion Pair in a Diffusion Chamber Model Amiodarone HCl and a tocol emulsion containing amiodarone and tocopherol phosphate as a tocol-soluble binary ion pair, prepared as mentioned above, were dialyzed against 20% glycerol, 3% Poloxamer 407 at pH 7.4 and 37° C.

The rate of free or complexed drug exiting the dialysis chamber provides an indirect estimate of the "sustained release" properties of the emulsion and the strength of the ion pair species. Rates of dialysis were linear with concentration for Amiodarone HCl, whereas diffusion for the amiodarone:tocopherol phosphate ion pair was negligible at the highest concentration tested. Given the low dielectric constant of the oil phase, this suggests the formation of a stable ion pair in the tocol emulsion.

Example 6

Tocotrienol Formulation for Vitamin E Succinate Co-Therapy

Given the potential therapeutic effect of Vitamin E succinic acid (VESA) in conjunction with xenotocols for the treatment of breast cancer and other cancers, there is a special need for multiphasic formulations that contain VESA in a tocotrienol oil. Here "vehicle" is taken in its customary meaning among pharmaceutical formulators to indicate the agent that carries the drug, the base formulation and excipients, particularly the oil phase thereof, without consideration of the active drug itself.

VESA and d-γ-tocotrienol were obtained from Eastman and the tocotrienol was further purified by vacuum distillation at about 30 milliTorr and 210° C. A final emulsion of 20 mg/mL VESA in 50 mg/mL of d-γ-tocotrienol and 12.5 mg/mL Capmul MCM as an oil phase was prepared using 30 mg/mL Poloxamer 407 as surfactant. PEG-400 was added to a final concentration of 5% before emulsification. Emulsification is performed as described in Examples 1 or 4, but may be more rapidly completed by increasing the temperature of emulsification to 70° C. or higher. Optionally, tocopheramine as the free base may be used to emulsify this oil mixture at lower temperature.

Example 7

Erythromycin Emulsion Compositions

Erythromycin (free base) solubility in α-tocopherol and medium-chain triglycerides (MCT) was determined to be approximately 10% and 4% w/w, respectively. Examples of emulsions incorporating erythromycin that were successfully prepared are shown in the table below.

Emulsions were prepared as described above. Emulsions A, B, C, and D were homogenized on the C5 to achieve microemulsions that were translucent and readily filter-sterilizable through a 0.2 $\mu$m membrane. The mean particle diameters of formulations A, B, and D were 47 nm, 48 nm, and 81 $\mu$n, Emulsion E was processed with the Virtis Handishear to produce a particle size of approximately 1.7 $\mu$m, and emulsion F was formed by simple stirring. All emulsions and microemulsions showed no sign of any crystallization or drug precipitation when examined visually and with a light microscope.

| Component | Component Function | A | B | C | D | E | F |
|---|---|---|---|---|---|---|---|
| | | (Weight %) | | | | | |
| Erythromycin | Active | 0.5 | 0.5 | 1.0 | 1.3 | 2.5 | 2.0 |
| Vitamin E Succinate | Ion pair forming Compound | 0.5 | | 1.0 | 1.0 | 1.8 | 1.5 |
| α-Tocopherol | Oil/Solvent | 8.0 | 8.0 | 8.0 | 7.1 | | |
| MCT | Oil/Solvent | | | | | 25.0 | 3.5 |
| TPGS | Surfactant | 5.0 | 5.0 | 5.0 | 4.5 | 5.0 | 3.5 |
| Poloxamer 407 | Surfactant | 1.0 | 1.0 | 1.0 | 0.9 | | |
| Water | Aqueous Phase | q.s. | q.s. | q.s. | q.s. | q.s. | q.s. |

Example 8

Conversion of Doxorubicin HCL to Free Base

Doxorubicin HCl in 8:1 $CHCl_3$: MeOH produced a drug suspension upon stirring under a stream of gaseous $NH_3$.

The resulting suspension was subsequently filtered to remove the insoluble material leaving behind a red solvent solution. It was subsequently dried down to a solid free base with an approximate recovery of 90% based on HPLC without any evidence of drug degradation.

Example 9

Tocol-soluble Doxorubicin Ion Pair Formation and Emulsion Composition

Vitamin E phosphate is supplied commercially as the sodium salt, so extraction into chloroform with acidic water was necessary to get the free acid, which was used to make an ion pair with doxorubicin free base at 2:1 molar ratio, which was soluble in vitamin E. This oil phase, when combined with the surfactant Tagat® TO (PEG-25 glyceryl trioleate), was readily emulsified at 60° C. with water by hand mixing to make a crude emulsion of the composition shown below with no evidence of drug precipitation. A fine emulsion can be prepared using high pressure homogenization to reduce particle size.

| Component | mg/mL |
|---|---|
| Doxorubicin (free base) | 0.3 |
| Vitamin E Phosphate | 0.6 |
| Vitamin E | 23.0 |
| Tagat TO | 23.8 |
| Water | qs |

Example 10

Alternative Doxorubicin Ion-Pairs and Emulsion Compositions

Using procedures analogous to those of Examples 8 and 9 ion-pairs of doxorubicin with vitamin E succinate, oleic acid, decyl and hexadecyl phosphates can be formed and incorporated in α-tocopherol emulsions. In addition to vitamin E and TPGS, poloxamers, polysorbates, lecithin, triglycerides, propylene glycol and polyethylene glycol can be included. Emulsion and drug stability can be controlled by optimizing the surfactant:ion pair:oil phase ratio.

Example 11

Tocopherolsuccinate-aspartate

Tocopherolsuccinate-aspartate is a novel compound that can be used to form ion pairs with cationic pharmaceutically active compounds used in this invention. Synthesis of the tocopherolsuccinate aspartate conjugate was carried out via the use of mixed anhydride chemistry. D-α-tocopherol succinate was activated by adding 1.2 equivalents of isobutylchloroformate (IBCF) and 1.4 equivalents of N-methylmorpholine (NMM) in a tetrahydrofuran (THF) medium at −5° C. To insure complete conversion to the mixed anhydride the reaction was stirred for 1 hour allowing the mixture to slowly warm to room temperature. The mixed anhydride was filtered to remove the N-methylmorpholine hydrochloride salt (NMM>HCl). The resulting filtrate was added drop-wise over 45 minutes to a −5° C. solution of 1.0 equivalence of L-aspartic acid dibenzyl ester p-toluenesulfonate salt and 1.5 equivalences of triethylamine (TEA) in THF solution over 1 hour. The reaction was allowed to continue for an additional 1 hr at −5° C., then warm to room temperature and was stirred for an additional 15 hours before isolating the product. Once the reaction was complete, the THF was removed in a vacuo to yield a crude yellow sticky solid. The product was dissolved in dichloromethane (DCM) and washed with 2×0.1 N HCl, 1×Sat. $NaHCO_3$, and 1×Sat. NaCl. The resulting organic mixture was dried over $MgSO_4$ and removed in a vacuo to yield an off white solid.

The tocopherolsuccinate-aspartate dibenzyl ester was deprotected by hydrogenation to yield the free diacid product. Total yield=72%. Purity=95%+by HPLC analysis. FT-IR: [N—H (amide), C=O (ester), C=O (amide), and C—O (ether) stretch] are 3336, 1736, 1645, 1153 cm$^{-1}$, respectively. The structure of tocopherolsuccinate-aspartate was confirmed by LC-MS.

Example 12

Tocopherolsuccinate-glutamate

Using the methodologies of Example 11, the novel compound tocopherolsuccinate-glutamate can readily be synthesized and characterized.

We claim:

1. A pharmaceutical composition comprising a tocol as a solvent, and a tocol soluble ion pair comprised of a charged pharmaceutically active compound or a charged precursor of a pharmaceutically active compound, and a compound of opposite charge capable of forming a tocol-soluble ion pair with the pharmaceutically active compound or precursor.

2. A composition according to claim 1 wherein the tocol is a tocopherol or tocotrienol.

3. A composition according to claim 1 wherein the tocol is a tocopherol.

4. A composition according to claim 3 wherein the tocopherol is α-tocopherol.

5. A composition according to claim 3 wherein the tocopherol is β-, γ- or δ-tocopherol.

6. A composition according to claim 1 wherein the tocol is a tocotrienol.

7. A composition according according to claim 1, wherein the tocol is selected from 6-hydroxy, 2,5,7,8-tetramethylchroman-2-carboxylic acid and its desmethyl analogs.

8. A composition according to claim 1 wherein the pharmaceutically active compound or precursor is selected from pharmaceutically active bases, acids, and natural and synthetic polyelectrolytes, and precursors thereof.

9. A composition according to claim 8 wherein the pharmaceutically active compound or precursor is selected from pharmaceutically active carboxylic acids, polycarboxylic acids, amines, polyamines, peptides, polypeptides, proteins, nucleotides, polynucleotides, saccharides, polysaccharides and charged polyelectrolytes, and precursors thereof.

10. A composition according to claim 9 wherein the pharmaceutically active compound or precursor is selected from pharmaceutically active amines, peptides and polypeptides, and precursors thereof.

11. A composition according to claim 10 wherein the pharmaceutically active compound is a macrolide antibiotic or a precursor thereof.

12. A composition according to claim 11 wherein the macrolide antibiotic is erythromycin or clarithromycin or a precursor thereof.

13. A composition according to claim 11 wherein the pharmaceutically active compound or precursor is an anti-arrhythmic drug or a precursor thereof.

14. A composition according to claim 13 wherein the anti-arrhythmic drug is amiodarone or a precursor thereof.

15. A composition according to claim 10 wherein the pharmaceutically active compound or precursor is an anthracycline antibiotic or a precursor thereof.

16. A composition according to claim 15 wherein the anthracycline antibiotic is doxorubicin, daunorubicin, epirubicin or a derivative thereof, or a precursor thereof.

17. A composition according to claim 10 wherein the pharmaceutically active agent or precursor is mitomycin, bleomycin or an analog thereof, or a precursor thereof.

18. A composition according to claim 10 wherein the pharmaceutically active compound or precursor is vincristine, vinblastine, a nitrogen mustard, nitrosourea, an analog thereof, or a precursor thereof.

19. A composition according to claim 10 wherein the pharmaceutically active compound or precursor is camptothecin, an analog thereof or a precursor thereof.

20. A composition according to claim 19 wherein the pharmaceutically active compound is camptothecin, topotecan, irenotecan, a derivative thereof, or a precursor thereof.

21. A composition according to claim 10 wherein the pharmaceutically active compound or precursor is a quinolone antibiotic or a precursor thereof.

22. A composition according to claim 21 wherein the quinolone antibiotic is ciprofloxacin, clinafloxacin, levofloxacin, moxifloxacin or a precursor thereof.

23. A composition according to claim 10 wherein the pharmaceutically active compound or precursor is a biogenic amine or a precursor thereof.

24. A composition according to claim 23 wherein the biogenic amine is histamine, serotonin, epinephrine, an analog thereof, or a precursor thereof.

25. A composition according to claim 1 in wherein the ion pair forming compound is selected from tocol derivatives, $C_2$–$C_{25}$ fatty acids, alkyl phosphates, lipids, phospholipids, retinoids, benzoquinones and esters of Vitamin A, D and K.

26. A composition according to claim 25 wherein the ion pair forming compound is a tocol derivative.

27. A composition according to claim 26 wherein the ion pair forming compound is a charged ester of α-tocopherol.

28. A composition according to claim 27 wherein the charged ester is selected from tocopherol acetate, phosphate, succinate, aspartate, and glutamate and mixtures thereof.

29. A composition according to claim 26 in which the ion pair forming compound is selected from amines of tocopherols and derivatives thereof.

30. A composition according to claim 29 wherein the ion pair forming compound is tocopheramine.

31. A composition according to claim 1 wherein the ion pair forming compound is selected from $C_2$–$C_{25}$ carboxylic acids, $C_2$–$C_{25}$ amines and mixtures thereof.

32. A composition according to claim 31 wherein the ion pair forming compound is selected from acetic, propionic, butyric, valeric, valproic, caprylic, caproic, lauric, myristic, palmitic, oleic, palmitoleic, stearic, linoleic, linolenic, arachidic and arachidonic acids, and mixtures thereof.

33. A composition according to claim 31 wherein the ion pair forming compound is stearylamine.

34. A composition according to claim 25 wherein the ion pair forming compound is selected from charged lipids, phospholipids, sphingolipids and mixtures thereof.

35. A composition according to claim 34 wherein the ion pair forming compound is a cholesterol analog or a mixture of cholesterol analogs.

36. A composition according to claim 35 wherein the ion pair forming compound is selected from cholesterol sulfate, cholesterol hemisuccinate, cholesterol succinate and mixtures thereof.

37. A composition according to claim 34 wherein the ion pair forming compound is a phospholipid or a mixture of phospholipids.

38. A composition according to claim 37 wherein the ion pair forming compound is selected from phosphatidic acid, phosphatidylserine, phosphatidylinositol, phosphatidylglycerol and diphosphatidylglycerol, and mixtures thereof.

39. A composition according to claim 34 wherein the ion pair forming compound is a sphingolipid or mixture of sphingolipids.

40. A composition according to claim 39 wherein the ion pair forming compound is selected from sphingosine, phosphatide analogs of sphingosine, and mixtures thereof.

41. A composition according to claim 39 wherein the ion pair forming compound is sphingomyelin.

42. A composition according to claim 1 wherein the pharmaceutically active compound is cationic and the ion pair forming compound is anionic.

43. A composition according to claim 42 wherein the ion pair forming compound is a succinate or phosphate derivative of a tocopherol.

44. A composition according to claim 42 wherein the pharmaceutically active compound is selected from erythromycin, clarithromycin, amiodarone, doxorubicin and cationic analogs thereof.

45. A composition according to claim 43 wherein the ion pair forming compound is selected from tocopherol succinate, tocopherol phosphate and mixtures thereof.

46. A composition according to claim 1 wherein the pharmaceutically active compound is anionic and the ion pair forming compound is cationic.

47. A composition according to claim 46 wherein the pharmaceutically active compound is a peptide, peptide mimetic, polypeptide, nucleotide or polynucleotide.

48. A composition according to claim 46 wherein the ion pair forming compound is tocopheramine, stearylamine, or sphingomyelin.

49. A composition according claim 1 in the form of a multiphase system.

50. A biphasic composition according to claim 49.

51. A composition according to claim 49 in the form of an emulsion or microemulsion.

52. A composition according to claim 49 comprising micelles, mixed micelles, reverse micelles, liposomes, niosomes and mixtures thereof.

53. A composition according to claim 49 comprising an oil-in-water or water-in-oil emulsion or microemulsion.

54. A composition according to claim 49 comprising an oil-in-water-in oil or water-in-oil-in-water emulsion or microemulsion.

55. A composition according to claim 49 further comprising one or more surfactants, one or more co-solvents and one or more aqueous phases.

56. A composition according to claim 1 in the form of a self-emulsifying drug delivery system.

57. A process for solubilizing in an oil phase a charged pharmaceutically active compound or a charged precursor thereof comprising combining the pharmaceutically active compound or precursor with an oppositely charged compound capable of forming a tocol-soluble ion pair with the pharmaceutically active compound or precursor, and with a tocol as a solvent for the ion pair.

58. A process according to claim 57 in which the oil phase is an oil phase of a multiphase system.

59. A composition according to claim 1 wherein the ion pair forming compound is tocopherolsuccinate-aspartate.

60. A composition according to claim 1 wherein the ion pair forming compound is tocopherolsuccinate-glutamate.

61. Pharmaceutical use of compositions of claim 1 by administration to an animal or human.

* * * * *

UNITED STATES PATENT AND TRADEMARK OFFICE
CERTIFICATE OF CORRECTION

PATENT NO. : 6,479,540 B1
DATED : November 12, 2002
INVENTOR(S) : P.P. Constantinides et al.

It is certified that error appears in the above-identified patent and that said Letters Patent is hereby corrected as shown below:

Title page,
Item [73], Assignee, "Seattle," should read -- Bothell, --
Item [56], References Cited, U.S. PATENT DOCUMENTS, ",858,398" should read -- 5,858,398 --

Column 14,
Line 37, "claim 1," should read -- claim 1 --

Column 15,
Line 29, "claim 1 in wherein" should read -- claim 1 wherein --

Column 16,
Line 45, "oil-in-water-in oil" should read -- oil-in-water-in-oil --

Signed and Sealed this

Seventeenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.  : 6,479,540 B1
DATED       : November 12, 2002
INVENTOR(S) : P.P. Constantinides et al.

It is certified that error appears in the above-identified patent and that said Letters Patent is hereby corrected as shown below:

Column 1,
Line 29, "(60 -tocopherol" should read -- α-tocopherol --
Line 43, "composition in which" should read -- composition in which --

Column 2,
Line 20, "5, 827,819; 5, 543,389;" should read -- 5,827,819; 5,543,389; --
Line 29, "In addition" should read -- In addition, --
Line 38, "active agent and" should read -- active agent, and --
Line 43, "compounds at least" should read -- compounds, at least --
Line 55, "example a cation" should read -- example, a cation --

Column 3,
Line 17, "phytylchroman" should read -- phytylchroman, --
Line 19, "is used herein" should read -- are used herein --
Line 25, "as a therapeutic agents." should read -- as therapeutic agents, --

Column 44,
Line 3, "i.e." should read -- i.e., --
Line 41, "10-100 nm" should read -- 10-100nm --
Line 63, "1:1 to 1:2"should read -- 1:1 to 1:2, --

Column 5,
Line 51, "antidepressants anxietolytics," should read -- antidepressants, anxietolytics, --

Column 6,
Line 4, "temazepam," should read -- ternazepam, --
Line 36, "for example" should read -- for example, --
Line 50, "example for" should read -- example, for --
Line 60, "For instance" should read -- For instance, --

Column 7,
Lines 39-40, "glyc
          erides" should break -- gly
          cerides --
Line 67, "Inown" should read -- known --

UNITED STATES PATENT AND TRADEMARK OFFICE
CERTIFICATE OF CORRECTION

PATENT NO. : 6,479,540 B1
DATED : November 12, 2002
INVENTOR(S) : P.P. Constantinides et al.

It is certified that error appears in the above-identified patent and that said Letters Patent is hereby corrected as shown below:

Column 8,
Line 32, "(DOGMA)," should read -- (DOTMA), --

Column 9,
Line 5, "Intravenous Administration." should read -- Intravenous Administration --
Line 35, "(Freeport Tenn.)." should read -- Freeport, Tenn.). --
Line 36, "(Janesville Wis.);" should read -- (Janesville, Wis.); --
Line 37, "(Parsippany N.J.,);" should read -- (Parsippany, N.J.); --
Line 38, "(Gardenia Calif.)," should read -- (Gardenia, Calif.), --
Line 39, "(St Louis MO)." should read -- (St Louis, Mo.). --

Column 10,
Line 4, "Ottawa Calif.)" should read -- Ottawa, Calif.). --
Line 16, "Santa Barbara Calif.)." should read -- Santa Barbara, Calif.). --
Line 47, "(St Louis MO)." should read -- (St Louis, Mo.). --
Line 58, Table, "d,1-a-tocopherol" should read -- d,1-a-tocopherol --

Column 12,
Line 23, "is performed" should read -- was performed --
Line 41, "81 µn," should read -- 81 nm, --
Line 47, before the table, insert "Erythromycin emulsion examples --

Column 13,
Line 2, "material leaving" should read -- ial, leaving --
Line 37, "9 ion" should read -- 9, ion --
Line 58, "mixed anhydride" should read -- mixed anhydride, --

UNITED STATES PATENT AND TRADEMARK OFFICE
CERTIFICATE OF CORRECTION

PATENT NO. : 6,479,540 B1
DATED : November 12, 2002
INVENTOR(S) : P.P. Constantinides et al.

It is certified that error appears in the above-identified patent and that said Letters Patent is hereby corrected as shown below:

Column 14,
Line 4, "2x0.1" should read -- 2X 0.1 --
Lines 4 and 5, "1xSat." should read -- 1X Sat. --
Line 9, "Purity=95%+by" should read -- Purity=95%+ by --

Signed and Sealed this

Seventeenth Day of August, 2004

JON W. DUDAS
*Acting Director of the United States Patent and Trademark Office*